United States Patent [19]

Levitt

[11] 4,293,330

[45] Oct. 6, 1981

[54] HERBICIDAL N-(PYRIDINYLAMINOCARBONYL)BENZENESULFONAMIDES

[75] Inventor: George Levitt, Wilmington, Del.

[73] Assignee: E. I. Du Pont de Nemours and Company, Wilmington, Del.

[21] Appl. No.: 192,034

[22] Filed: Sep. 29, 1980

Related U.S. Application Data

[63] Continuation-in-part of Ser. No. 82,522, Oct. 9, 1979, abandoned.

[51] Int. Cl.[3] .................. A01N 43/40; C07D 213/28; C07D 213/86
[52] U.S. Cl. ...................................... 71/94; 546/292; 546/306
[58] Field of Search .................... 71/94; 546/292, 306

[56] References Cited

U.S. PATENT DOCUMENTS

| | | | |
|---|---|---|---|
| 2,977,375 | 3/1961 | Haack et al. | 564/42 |
| 4,127,405 | 11/1978 | Levitt | 71/93 |
| 4,193,788 | 3/1980 | Shudo et al. | 546/305 |
| 4,221,585 | 9/1980 | Levitt | 71/92 |

OTHER PUBLICATIONS

Holland, The Journal of Organic Chemistry, vol. 26, pp. 1662–1665, (1961).

*Primary Examiner*—Alan L. Rotman

[57] ABSTRACT

N-(Pyridinylaminocarbonyl)benzenesulfonamides are useful for the regulation of plant growth and as pre-emergence and post-emergence herbicides.

24 Claims, No Drawings

HERBICIDAL N-(PYRIDINYLAMINOCARBONYL)BENZENESULFONAMIDES

RELATED APPLICATION

This application is a continuation-in-part of my copending application U.S. Ser. No. 082,522, filed Oct. 9, 1979, now abandoned.

BACKGROUND OF THE INVENTION

This invention relates to novel N-(pyridinylaminocarbonyl)benzenesulfonamides. The compounds of this invention and their agriculturally suitable salts, are useful as agricultural chemicals, e.g., plant growth regulants and herbicides.

There are a number of references to compounds with the general formula:

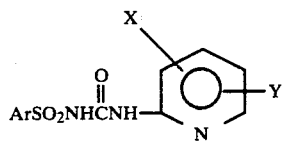

in the literature.

German Pat. No. 1,117,103 (Feb. 11, 1953) discloses

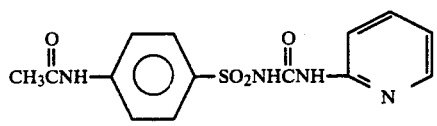

as a pharmaceutical intermediate.

Logemann, W.; Caprio, W.; and Artini, D; Farmaco (Pavia), Ed. Sci. 12, 589 (1956) discloses the synthesis of

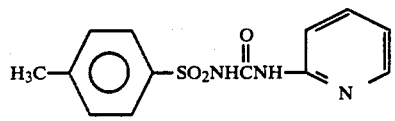

which was treated as a hypoglycemic agent.

German Pat. No. 1,012,598 (July 25, 1957) discloses the following as blood sugar lowering and bacteriostatic agents:

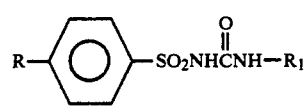

R = $NH_2$ or $NO_2$; $R_1$ = 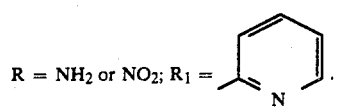

Ruschig, H. et al., Arzneimitt-Foroch, 8, 448 (1958) reports on blood sugar reducing agents:

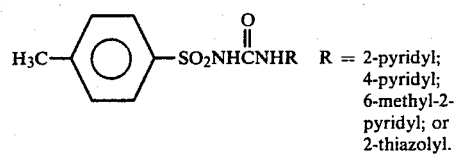

R = 2-pyridyl; 4-pyridyl; 6-methyl-2-pyridyl; or 2-thiazolyl.

U.S. Pat. No. 2,977,375 (Mar. 28, 1961) and British Pat. No. 797,474 (July 2, 1958) disclose the same subject matter as in German Pat. No. 1,012,598 mentioned above.

Onishi, S., Yakugaku Zasski 79, 559 (1959) discloses the following, tested as hypoglycemics;

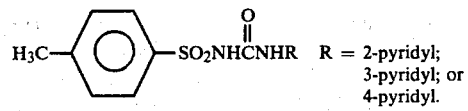

R = 2-pyridyl; 3-pyridyl; or 4-pyridyl.

Holland, G. F., J. Org. Chem., 26, 1662 (1961) discloses compounds of the following strucutre tested as antidiabetics.

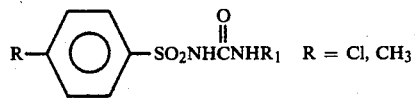

R = Cl, $CH_3$

$R_1$ = 4-picolyl or 6-methyl-2-picolyl.

Brzozowski, Z., Zh. Obsch. Khem., 39, 430 (1969) discloses aniline complexes of the following:

R = 2-pyridyl or 4-pyridyl.

No use was disclosed.

Brzozowski, Z., Rocz. Chem., 43, 1761 (1961) discloses the synthesis of:

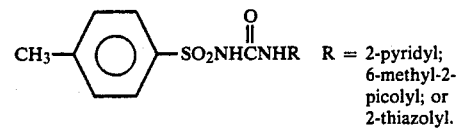

R = 2-pyridyl; 6-methyl-2-picolyl; or 2-thiazolyl.

German Pat. No. 2,205,194 (Aug. 24, 1972) discloses cardiovascular, hypertensive analgesic and antiinflammatory drugs, CNS stimulants and antispasmodics.

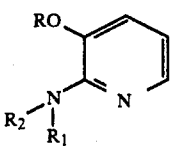

wherein
$R_1$ = alkylphenylsulfonamido;
$R_2$ = H or alkyl; and

R=H, carbamoyl, acyl, or arylsulfonyl.

Abon Ouf, A. A., et al., *J. Drug. Res.*, 6, 123 (1974) discloses the following as being related to antidiabetic drugs.

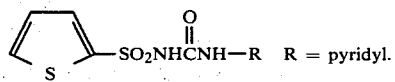

R = pyridyl.

The presence of undesired vegetation causes substantial damage to useful crops, especially agricultural products that satisfy man's basic food and fiber needs, such as cotton, rice, corn, wheat and the like. The current population explosion and concomitant world food and fiber shortage demand improvements in the efficiency of producing these crops. Preventing or minimizing loss of a portion of such valuable crops by killing or inhibiting the growth of undesired vegetation is one way of improving this efficiency. A wide variety of materials useful for killing or inhibiting (controlling) the growth of undesirable vegetation is available; such materials are commonly referred to as herbicides. The need still exists; however, for more effective herbicides.

SUMMARY OF THE INVENTION

According to this invention, there are provided novel compounds of formula I and their agriculturally suitable salts, e.g., Na, K, alkylammonium, trichloroacetic acid, suitable agricultural compositions containing them and methods of using them as general or selective pre-emergence and post-emergence herbicides and as plant growth regulators:

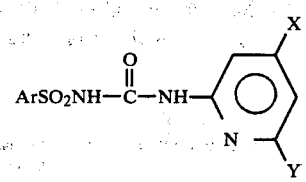

wherein

X is $CH_3-$, $CH_3CH_2-$ or $CH_3O$;

Y is $CH_3-$, $CH_3CH_2-$, $CH_3O-$, $CH_3CH_2O-$, Cl, Br or F;

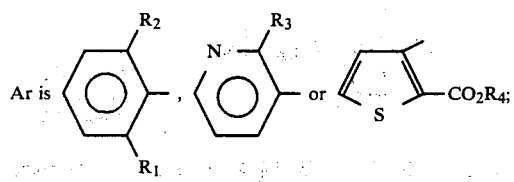

$R_1$ is $CO_2R_4$, $CF_3$, $NO_2$, Cl, $R_5SO_2-$ or $R_6R_7NSO_2-$;

$R_2$ is H, Cl or $CH_3$;

$R_3$ is Cl;

$R_4$ is $C_1-C_4$ alkyl, $C_3-C_4$ alkenyl, $ClCH_2CH_2-$ or $CH_3OCH_2CH_2-$;

$R_5$ is $C_1-C_4$ alkyl;

$R_6$ and $R_7$ are independently $CH_3-$ or $CH_3CH_2-$; provided that when $R_2$ is Cl or $CH_3-$, $R_1$ must be Cl or $NO_2$;

when $R_1$ is $CF_3$, $NO_2$ or Cl, then X and Y are independently $CH_3-$ or $CH_3O-$.

Preferred independently for their ease of synthesis are those compounds of Formula I wherein:

(1) $R_1$ is $R_6R_7NSO_2-$, $R_5SO_2-$, $CO_2R_4$ wherein $R_4$ is $C_1-C_3$ alkyl or allyl, or;

(2) $R_1$ is $NO_2$ and $R_2$ is Cl.

Equally preferred for their ease of synthesis are those compounds of Formula I wherein:

(3) Y is Cl, Br, $CH_3-$ or $CH_3O-$.

More preferred are those compounds of preferred (1) wherein:

(4) Y is Cl, Br, $CH_3-$ or $CH_3O-$.

Specifically preferred for ease of synthesis are the compounds:

2-[[(4,6-dimethyl-2-pyridinyl)aminocarbonyl]aminosulfonyl]benzoic acid, methyl ester;

2-[[(6-methoxy-4-methyl-2-pyridinyl)aminocarbonyl]aminosulfonyl]benzoic acid, methyl ester;

2-[[(6-bromo-4-methyl-2-pyridinyl)aminocarbonyl]aminosulfonyl]benzoic acid, methyl ester; and N'-[(4,6-dimethyl-2-pyridinyl)aminocarbonyl]-N,N-dimethyl-1,2-benzenedisulfonamide.

Synthesis

As shown in Equation 1, the compounds of formula I can be prepared by combining an appropriate 2-aminopyridine of formula III with an appropriately substituted sulfonyl isocyanate of formula II; Ar, X and Y being as previously defined.

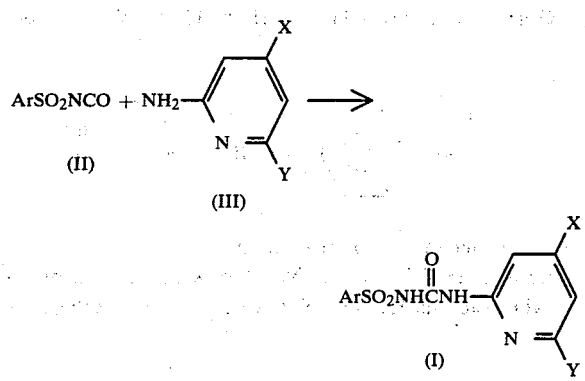

The reaction is best carried out in inert aprotic organic solvents such as methylene chloride, tetrahydrofuran or acetonitrile, at ambient pressure and temperature. The mode of addition is not critical; however, it is often convenient to add the sulfonyl isocyanate to a stirred suspension of the aminopyridine. Since such isocyanates usually are liquids, their addition is more easily controlled.

The reaction is generally exothermic. In some cases, the desired product is insoluble in the warm reaction medium and crystallizes from it in pure form. Products soluble in the reaction medium are isolated by evaporation of the solvent, trituration of the solid residue with solvents such as 1-chlorobutane, ethyl ether, or pentane, and filtration.

The intermediate sulfonyl isocyanates of formula II can be prepared by reacting corresponding sulfonamides with phosgene in the presence of n-butyl isocyanate at reflux in a solvent such as chlorobenzene, according to the procedure of H. Ulrich and A. A. Y. Sayigh, *Newer Methods of Preparative Organic Chemistry*, Vol. VI p. 223-241, Academic Press, New York and London, W. Foerst Ed. In cases where formation of the desired sulfonyl isocyanate is difficult by the above procedure the sulfonyl urea formed by reaction of butyl isocyanate with the appropriate sulfonamide is treated with phosgene according to the above reference.

Some of the sulfonyl isocyanates used in this invention are novel. The synthesis of these intermediates is described in my co-pending applications U.S. Ser. No. 029,281 filed Apr. 13, 1979, U.S. Ser. No. 083,753 filed Oct. 22, 1979, and U.S. Ser. No. 098,723 filed Nov. 30, 1979, the disclosure of which is herein incorporated by reference.

These intermediates are prepared from the parent sulfonamides of formula IV as shown in Equation II by reaction with phosgene as described above or in my copending application.

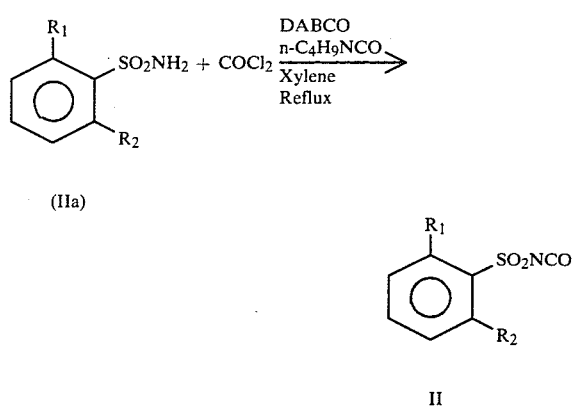

A mixture of the appropriate sulfonamide, IIa, an alkyl isocyanate such as butyl isocyanate and a catalytic amount of 1,4-diaza[2,2,2]bicyclooctane (DABCO) in xylene, chlorobenzene or other inert solvent of sufficiently high boiling point (e.g. >135°) is heated to approximately 135°. Phosgene is added to the mixture until an excess of phosgene is present as indicated by a drop in the boiling point. (The mixture is heated further to drive off the excess phosgene). After the mixture is cooled and filtered to remove a small amount of insoluble by-products, the solvent and alkyl isocyanate are distilled off in-vacuo leaving a residue which is the crude sulfonyl isocyanate II.

In Equation II, $R_1$ and $R_2$ are as previously defined.

The preparation of sulfonamides from ammonium hydroxide and sulfonyl chlorides is widely reported in the literature, e.g. Crossley et al., *J. Am. Chem. Soc.* 60, 2223 (1938).

Certain sulfonyl chlorides are best prepared by chlorosulfonation of a substituted benzene according to the teaching of H. T. Clarke, et al., *Org. Synth.* Coll. Vol. 1, 2nd Ed. 1941, p. 85. Other benzenesulfonyl chlorides are best made by diazotization of the appropriate aniline with sodium nitrite in HCl, followed by reaction of the diazonium salt with sulfur dioxide and cuprous chloride in acetic acid according to the teaching of H. L. Yale and F. Sowinski, *J. Org. Chem.* 25, 1824 (1960).

N,N-Dialkyl-o-sulfamoylbenzenesulfonyl isocyanates are important intermediates for the preparation of certain of the compounds of this invention. The synthesis of the sulfonamide intermediates required for these sulfonyl isocyanates is described in Equation III.

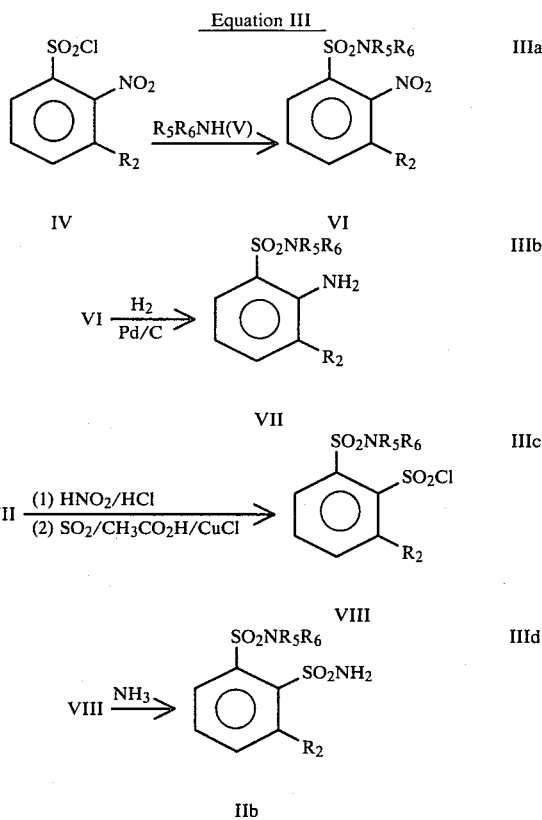

wherein
$R_2$, $R_5$ and $R_6$ are as previously defined.

In step IIIa, the o-nitrobenzenesulfonyl chloride in formula IV, which are well-known in the art, are contacted with an amine of formula V in an inert organic solvent such as methylene chloride, ethyl ether, or tetrahydrofuran at 0°–50°. The amine V may be taken in excess to act as an acid acceptor; or, alternatively, a tertiary amine such as triethylamine or pyridine may be used as an acid acceptor. The by-product amine hydrochloride is filtered off or washed out of the solvent with water and the product isolated by evaporation of the solvent.

The reduction described in step IIIb is accomplished by treating a solution of the compounds of formula VI, in a solvent such as ethanol, ethyl acetate, or DMF, in a pressure vessel, with 100–1000 pounds per square inch or hydrogen at 80°–150° in the presence of a hydrogenation catalyst such as 5–10% palladium absorbed on carbon. When the theoretical amount of hydrogen has been absorbed, the solution is cooled and the catalyst is removed by filtration. The product is then isolated by evaporation of the solvent.

The diazotization and coupling with sulfur dioxide, described in step IIIc, is accomplished in the following manner. A solution of the o-sulfamoyl aniline of formula VII in a mixture of concentrated hydrochloric acid and glacial acetic acid is treated with a solution of sodium nitrite in water at −5° to 0°. After stirring for 10–15 minutes at 0° to insure complete diazotization, this solution is added to a mixture of an excess of sulfur dioxide, and a catalytic amount of cuprous chloride in glacial acetic acid at 0°–5°. The temperature is kept at 0°–5° for ¼ to 1 hour then raised to 20°–25° and held at that temperature for 2–4 hours. This solution is then poured into a large excess of ice water. The sulfonyl chloride products, VIII, can be isolated by filtration or by extraction into a solvent such as ethyl ether or methylene chloride followed by evaporation of the solvent.

The amination described in step IIId is conveniently carried out by treating a solution of the sulfonyl chloride of formula VIII with an excess of anhydrous ammonia in a solvent such as ethyl ether or methylene chloride at 0°–25°. If the product sulfonamide, IIb, is insoluble it may be isolated by filtration followed by washing out the salts with water. If the product sulfonamide is soluble in the reaction solution, it may be isolated by filtering off the precipitated ammonium chloride and evaporation of the solvent.

The synthesis of aminoheterocyclics has been reviewed in "The Chemistry of Heterocyclic Compounds," a series published by Interscience Publ., New York and London. 2-Aminopyridines are described in the volumes of this series entitled "Pyridine and Its Derivatives", 1962, edited by E. Klingsberg.

2-Amino-6-bromo-4-methylpyridine and similarly substituted pyridines can be made by the cyclization of the corresponding dinitrile according to the teachings of F. Johnson, J. P. Panilla, A. A. Carlson and D. H. Hunneman (*J. Org. Chem.* 27 2473 (1962)).

Agriculturally suitable salts of compounds of formula I are also useful herbicides and can be prepared in a number of ways known to the art. For example, metal salts can be made by contacting compounds of formula I with a solution of an alkali or alkaline earth metal salt having a sufficiently basic anion (e.g. hydroxide, alkoxide, carbonate or hydride). Quaternary amine salts can be made by similar techniques.

Salts of compounds of formula I can also be prepared by exchange of one cation for another. Cationic exchange can be effected by direct contact of an aqueous solution of a salt of a compound of formula I (e.g. alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of formula I (e.g. an alkali metal or quaternary amine salt) through a column packed with a cation exchange resin containing the cation to be exchanged. In this method, the cation of the resin is exchanged for that of the original salt and the desired produce is eluted from the column. This method is particularly useful when the desired salt is water-soluble.

Acid addition salts, useful in this invention, can be obtained by reacting a compound of formula I with a suitable acid, e.g. p-toluenesulfonic acid, trichloroacetic acid or the like.

The compounds of this invention and their preparation are further illustrated by the following examples wherein temperatures are given in degrees centigrade and parts are by weight unless otherwise designated.

EXAMPLE 1 o-Nitro-N,N-diethylbenzenesulfonamide

To a solution of 132.6 g of o-nitrobenzenesulfonyl chloride in 700 ml of tetrahydrofuran was added 88.5 g of diethylamine at 5°–15°. The reaction mixture was stirred at room temperature for 1 hour before the precipitated diethylamine hydrochloride was removed by filtration. The filtrate was evaporated to dryness in-vacuo and the residue dissolved in 1-chlorobutane. The 1-chlorobutane solution was washed with water, dried over magnesium sulfate and evaporated in-vacuo to give 122.4 g of o-nitro-N,N-diethylbenzenesulfonamide as a dark oil.

NMR(CDCl$_3$)δ: 1.1-1.4 [t, 6.1H, (CH$_3$CH$_2$)$_2$N-]; 3.3-3.8 [qt, 3.8H, (CH$_3$CH$_2$)$_2$N-]; 8.0-8.6 (m, 4.1H, 4 aromatics).

EXAMPLE 2 o-Amino-N,N-diethylbenzenesulfonamide

In a pressure vessel a mixture of 133 g of o-nitro-N,N-diethylbenzenesulfonamide, 5 g of 10% palladium on carbon, and 500 ml of ethyl acetate was shaken at 130° under 500 psi hydrogen pressure until hydrogen was no longer absorbed. The reaction mixture was cooled and the catalyst filtered off. Evaporation of the solvent in-vacuo gave 123 g of o-amino-N,N-diethylbenzenesulfonamide as a viscous oil which slowly crystallized to a solid, m.p. 45°–51°.

NMR(CDCl$_3$)δ: 1.0-1.3 [t, 6.7H, (CH$_3$CH$_2$)$_2$N-]; 3.0-3.5 [qt, 3.6H, (CH$_3$CH$_2$)$_2$N-]; 4.8-5.2 (broad, 1.7H, NH$_2$); 6.5-7.7 (m, 4.0H, 4 aromatics).

EXAMPLE 3

N,N-Diethyl-1,2-benzenedisulfonamide

To a solution of 114 g of o-amino-N,N-diethylbenzenesulfonamide in a mixture of 400 ml of concentrated hydrochloric acid and 100 ml of glacial acetic acid was added a solution of 50 g of sodium nitrite in 130 ml of water at −5° to 0°. The solution was stirred at 0° for 15 minutes then poured into a mixture of 14 g of cuprous chloride and 100 ml of liquid sulfur dioxide in 550 ml of glacial acetic acid at 0°–5°. This mixture was stirred at 0° for 15 minutes then at room temperature for 3 hours before pouring into three liters of ice water. The crude suflonyl chloride was filtered off and washed with water. It was then dissolved in 1 l of ethyl ether, washed with water and dried over magnesium sulfate. To this ether solution was added 20 ml of liquid anhydrous ammonia at 5°–15°. After stirring overnight at room temperature the solid was filtered off, washed with water, ethanol and then 1-chlorobutane, Oven drying at 60° gave 91.8 g N,N-diethyl-1,2-benzenedisulfonamide, m.p. 156°–9°.

NMR(DMSO)δ: 0.9-1.2 [t, 6.0H, (CH$_3$CH$_2$)$_2$N-]; 3.2-3.6 [qt, 3.8H, (CH$_3$CH$_2$)$_2$N-]; ~7.2 (broad singlet, 2.1H, NH$_2$); 7.7-8.4 (m, 4.1H, 4 aromatics).

EXAMPLE 4 o-N,N-Diethylsulfamoylbenzenesulfonyl isocyanate

A solution of 13.2 g of N,N-diethyl-1,2-benzenedisulfonamide, 4.5 g of n-butylisocyanate, and 0.2 g of 1,4-diaza[2,2,2]bicyclooctane (DABCO) in 90 ml of mixed xylenes was heated to 135°. To this solution was added 3.3 ml of liquid phosgene at such a rate that the temperature was maintained between 125 and 135° (about 2 hours). The temperature was kept at 130° for ½ hour after the addition. The solution was cooled and filtered to remove a small amount of insoluble solid then concentrated at 60°–70° in-vacuo. The residue of o-N,N-diethylsulfamoylbenzenesulfonyl isocyanate was an oil weighing 16.8 g and was sufficiently pure for further reaction.

EXAMPLE 5

Methyl 2-(isocyanatosulfonyl)benzoate

A stirred mixture containing 157 g of methyl 2-sulfamoylbenzoate, 73 g of butyl isocyanate 0.3 g of 1,4-diazabicyclo[2,2,2]octane and 1.0 l of xylene was heated to reflux for one half hour. Phosgene gas was then passed into the system under a dry ice reflux condenser allowing the reaction temperature to drop to 120°. This addition was continued until the reflux temperature remained at 120° without further phosgene addition. The temperature of the reaction mixture was then raised to 136° (by removal of the dry ice reflux condenser) after which it was cooled to room temperature and filtered. Evaporation of the filtrate yielded the desired crude sulfonyl isocyanate which could be purified by distillation at 132°–138° C. under 1.0 to 1.1 mm of mercury pressure. The product is extremely reactive with water so contact with moisture should be scrupulously avoided.

EXAMPLE 6

2-[[(4,6-dimethyl-2-pyridinyl)aminocarbonyl]aminosulfonyl]benzoic acid, methyl ester To 1.2 g of 2-amino-4,6-dimethylpyridine in 30 ml of methylene chloride at ambient temperature was added dropwise, with stirring 2.4 g of methyl 2-isocyanatosulfonylbenzoate. After stirring for one hour at room temperature a solid precipitated from the mixture. Filtration yielded 1.8 g of a crystalline white solid which melted at 181°–182° C. and showed absorption peaks by infrared spectroscopy at 1750, 1700, 1630 and 1580 cm$^{-1}$. The nuclear magnetic resonance spectrum (60 mc) showed peaks at 7-8.6 δ (multiplet) for o-substituted benzene, 4.36 δ (singlet) for OCH$_3$ and 2.76, 2.7 δ (singlets) for the two methyl groups on the pyridine ring.

By using the procedure of Example 6 and substituting equivalent amounts of an appropriately substituted arylsulfonyl isocyanate and aminopyridine, the following compounds are prepared.

TABLE I

| $R_1$ | $R_2$ | X | Y | m.p. (°C.) |
|---|---|---|---|---|
| CO$_2$CH$_3$ | H | CH$_3$ | CH$_3$ | 181–182° |
| CO$_2$CH$_2$CH$_3$ | H | CH$_3$ | CH$_3$ | |
| CO$_2$CH$_2$CH$_2$CH$_3$ | H | CH$_3$ | CH$_3$ | |
| CO$_2$CHCH$_3$<br>\|<br>CH$_3$ | H | CH$_3$ | CH$_3$ | |
| CO$_2$CH$_2$CH$_2$CH$_2$CH$_2$ | H | CH$_3$ | CH$_3$ | |
| CO$_2$CH—CH$_2$CH$_3$<br>\|<br>CH$_2$ | H | CH$_3$ | CH$_3$ | |
| CO$_2$—CH$_2$CH=CH$_2$ | H | CH$_3$ | CH$_3$ | |
| CO$_2$—CH$_2$CH=CH$_2$CH$_3$ | H | CH$_3$ | CH$_3$ | |
| CO$_2$CH$_2$CH$_2$Cl | H | CH$_3$ | CH$_3$ | |
| CO$_2$CH$_2$CH$_2$OCH$_3$ | H | CH$_3$ | CH$_3$ | |
| CF$_3$ | H | CH$_3$ | CH$_3$ | |
| NO$_2$ | H | CH$_3$ | CH$_3$ | 162° (d) |
| Cl | H | CH$_3$ | CH$_3$ | |
| SO$_2$CH$_3$ | H | CH$_3$ | CH$_3$ | |
| SO$_2$CH$_2$CH$_3$ | H | CH$_3$ | CH$_3$ | |
| SO$_2$CH$_2$CH$_2$CH$_3$ | H | CH$_3$ | CH$_3$ | 188–189° |
| SO$_2$CH—CH$_3$<br>\|<br>CH$_3$ | H | CH$_3$ | CH$_3$ | |
| SO$_2$CH$_2$CH$_2$CH$_2$CH$_3$ | H | CH$_3$ | CH$_3$ | |
| SO$_2$CH$_2$CH$_2$CH$_3$<br>\|<br>CH$_3$ | H | CH$_3$ | CH$_3$ | |
| SO$_2$N(CH$_3$)$_2$ | H | CH$_3$ | CH$_3$ | 204–210° |
| SO$_2$NCH$_3$<br>\|<br>CH$_2$CH$_3$ | H | CH$_3$ | CH$_3$ | |
| SO$_2$N(CH$_2$CH$_3$)$_2$ | H | CH$_3$ | CH$_3$ | |
| Cl | Cl | CH$_3$ | CH$_3$ | |
| Cl | CH$_3$ | CH$_3$ | CH$_3$ | |
| NO$_2$ | CH$_3$ | CH$_3$ | CH$_3$ | |
| NO$_2$ | Cl | CH$_3$ | CH$_3$ | |
| CO$_2$CH$_3$ | H | CH$_3$ | OCH$_3$ | 184–187° |
| CO$_2$CH$_3$ | H | CH$_3$ | Br | 210–211° |
| CO$_2$CH$_3$ | H | CH$_2$CH$_3$ | Br | 136–140° |
| CO$_2$CH$_3$ | H | CH$_2$CH$_3$ | OCH$_3$ | 184–188° |
| CO$_2$CH$_3$ | H | OCH$_3$ | OCH$_3$ | |
| CO$_2$CH$_3$ | H | CH$_3$ | OCH$_2$CH$_3$ | |
| CO$_2$CH$_3$ | H | CH$_3$ | Cl | |
| CO$_2$CH$_3$ | H | CH$_3$ | F | |
| CO$_2$CH$_3$ | H | CH$_2$CH$_3$ | CH$_2$CH$_3$ | |
| SO$_2$N(CH$_3$)$_2$ | H | OCH$_3$ | CH$_3$ | |
| SO$_2$N(CH$_3$)$_2$ | H | OCH$_3$ | CH$_2$CH$_3$ | |

TABLE II

| $R_3$ | X | Y | m.p. (°C.) |
|---|---|---|---|
| Cl | CH$_3$ | CH$_3$ | 149–155° |
| Cl | CH$_3$ | OCH$_3$ | |
| Cl | CH$_3$ | Br | |
| Cl | CH$_2$CH$_3$ | CH$_3$ | |
| Cl | CH$_2$CH$_3$ | OCH$_3$ | |
| Cl | CH$_2$CH$_3$ | Br | |
| Cl | OCH$_3$ | OCH$_3$ | |
| Cl | OCH$_3$ | CH$_3$ | |
| Cl | CH$_3$ | Cl | |
| Cl | CH$_2$CH$_3$ | CH$_2$CH$_3$ | |

TABLE III

[Structure: thiophene with SO₂NHCONH-pyridine(X,Y substituents) and CO₂R₄ group]

| R₄ | X | Y |
|---|---|---|
| CH₃ | CH₃ | CH₃ |
| CH₂CH₃ | CH₃ | CH₃ |
| CH₂CH₂CH₃ | CH₃ | OCH₃ |
| CH₂CH₃<br>\|<br>CH₃ | CH₃ | OCH₃ |
| CH₂CH₂CH₂CH₃ | CH₃ | Br |
| CH₂CHCH₃<br>\|<br>CH₃ | CH₂CH₃ | OCH₃ |
| CHCH₂CH₃<br>\|<br>CH₃ | CH₂CH₃ | Br |

Formulations

Useful formulations of the compounds of Formula I can be prepared in conventional ways. They include dusts, granules, pellets, suspensions, emulsions, wettable powders, emulsifiable concentrates and the like. Many of them can be applied directly. Sprayable formulations can be extended in suitable media and used at spray volumes of from a few liters to several hundred liters per hectare. High strength compositions are used primarily as concentrates which are to be diluted prior to ultimate use. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the approximate proportions set forth in Table II.

TABLE IV

| | Weight Percent* | | |
|---|---|---|---|
| | Active Ingredient | Diluent(s) | Surfactant(s) |
| Wettable Powders | 20–90 | 0–74 | 1–10 |
| Oil Suspensions, Solutions Emulsions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active Ingredient plus at least one of a Surfactant or a Diluent equals 100 weight percent.

Lower or higher levels of active ingredient can be present, depending on the intended use and the physical properties of the compound. Higher ratios of surfactant to active ingredient are sometimes desirable, and are achieved by incorporation into the formulation, or by tank mixing.

Some typical solid diluents are described in Watkins, et al., "Handbook of Insecticide Dust Diluents and Carriers", 2nd Ed., Dorland Books, Caldwell, New Jersey, but other solids, either mined or manufactured, may be used. The more absorptive diluents are preferred for wettable powders and the denser ones for dusts. Typical liquid diluents and solvents are described in Marsden, "Solvents Guide", 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, New Jersey, as well as Sisely and Wood, "Encyclopedia of Surface Active Agents", Chemical Publishing Co., Inc. New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending, and usually grinding, as in a hammer or fluid energy mill. Suspensions are prepared by wet milling (see, for example, Littler, U.S. Pat. No. 3,060,084). Granules and pellets can be made by spraying the active material on preformed granular carriers or by agglomeration techniques. See J. E. Browning, "Agglomeration", *Chemical Engineering*, Dec. 4, 1967, pp. 147ff. and "Perry's Chemical Engineer's Handbook", 4th Ed., McGraw-Hill, New York, 1963, pp. 8–59ff.

For further information regarding the art of formulation, see for example:

H. M. Loux, U.S. Pat. No. 3,235,361, Col. 6, line 16 through Col. 7, line 19 and Examples 10 through 41.

R. W. Luckenbaugh, U.S. Pat. No. 3,309,192, Col. 5, line 43 through Col. 7, line 62 and Examples 8, 12, 15, 39, 41, 52, 53, 58, 132, 138–140, 162–164, 166, 167, 169–182.

H. Gysin and E. Knusli, U.S. Pat. No. 2,891,855, Col. 3, line 66 through Col. 5, line 17 and Examples 1–4.

G. C. Klingman, "Weed Control as a Science", John Wiley & Sons, Inc., New York, 1961, pp. 81–96. J. D. Fryer and S. A. Evans, "Weed Control Handbook", 5th Ed., Blackwell Scientific Publications, Oxford, 1968, pp. 101–103.

Unless indicated otherwise, all parts are by weight in the following examples.

EXAMPLE 7

| Wettable Powder | |
|---|---|
| 2-[[4,6-dimethyl-2-pyridinyl)-aminocarbonyl]aminosulfonyl]-benzoic acid, methyl ester | 80% |
| sodium alkylnaphthalenesulfonate | 2% |
| sodium ligninsulfonate | 2% |
| synthetic amorphous silica | 3% |
| kaolinite | 13% |

The ingredients are thoroughly blended and hammer milled to produce particles essentially all below 50 microns. The product is reblended and sifted through a U.S.S. No. 50 sieve (0.3 mm opening) before packaging.

EXAMPLE 8

| Wettable Powder | |
|---|---|
| 2-[[4,6-dimethyl-2-pyridinyl)-aminocarbonyl]aminosulfonyl]-benzoic acid, methyl ester | 50% |
| sodium alkylnaphthalenesulfonate | 2% |
| low viscosity methyl cellulose | 2% |
| diatomaceous earth | 46% |

The ingredients are blended, coarsely hammer milled and then air milled to produce particles of active essentially all below 10 microns in diameter. The product is reblended before packaging.

EXAMPLE 9

| Granule | |
| --- | --- |
| wettable powder of Example 8 | 10% |
| attapulgite granules (U.S.S. #20–40; 0.84–0.42 mm) | 90% |

A slurry of wettable powder containing 50% solids is sprayed on the surface of attapulgite granules in a double-cone blender. The granules are dried and packaged.

EXAMPLE 10

| Oil Suspension | |
| --- | --- |
| 2-[[4,6-dimethyl-2-pyridinyl)-aminocarbonyl]aminosulfonyl]-benzoic acid, methyl ester | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 11

| Wettable Powder | |
| --- | --- |
| 2-[[4,6-dimethyl-2-pyridinyl)-aminocarbonyl]aminosulfonyl]-benzoic acid, methyl ester | 65% |
| dodecylphenol polyethylene glycol ether | 2% |
| sodium ligninsulfonate | 4% |
| sodium silicoaluminate | 6% |
| montmorillonite (calcined) | 23% |

The ingredients are thoroughly blended. The liquid surfactant is added by spraying upon the solid ingredients in the blender. After grinding in a hammer mill to produce particles essentially all below 100 microns, the material is reblended and sifted through a U.S.S. No. 50 sieve (0.3 mm opening) and packaged.

EXAMPLE 12

| High Strength Concentrate | |
| --- | --- |
| 2-[[4,6-dimethyl-2-pyridinyl)-aminocarbonyl]aminosulfonyl]-benzoic acid, methyl ester | 98.5% |
| silica aerogel | 0.5% |
| synthetic amorphous fine silica | 1.0% |

The ingredients are blended and ground in a hammer mill to produce a high strength concentrate essentially all passing a U.S.S. No. 50 sieve (0.3 mm openings). This material may then be formulated in a variety of ways.

EXAMPLE 13

| Extruded Pellet | |
| --- | --- |
| 2-[[4,6-dimethyl-2-pyridinyl)-aminocarbonyl]aminosulfonyl]-benzoic acid, methyl ester | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 14

| Wettable Powder | |
| --- | --- |
| 2-[[( 4,6-dimethyl-2-pyridinyl)-aminocarbonyl]aminosulfonyl]-benzoic acid, methyl ester | 40% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended, passed through an air mill, to produce an average particle size under 15 microns, reblended, and sifted through a U.S.S. No. 50 sieve (0.3 mm opening) before packaging.

All compounds of the invention may be formulated in the same manner.

Utility

The compounds of formula I are useful as herbicides. They may be applied either pre- or post-emergence for the control of undesired vegetation in noncrop areas or for selective weed control in certain crops, e.g., wheat. Some of these compounds are useful for the pre- and/or post-emergence control of nutsedge. By properly selecting rate and time of application, compounds of this invention may be used to modify plant growth beneficially.

The precise amount of the compound of formula I to be used in any given situation will vary according to the particular end result desired, the use involved, the weeds to be controlled, the soil type, the formulation and mode of application, weather conditions, etc. Since so many variables play a role, it is not possible to state a rate of application suitable for all situations. Broadly speaking, the compounds of this invention are used at levels of about 0.01 to 20 kg/ha with a preferred range of 0.05 to 10 kg/ha. The lower rates of the range will generally be selected for lighter soils, for selective weed control in crops, or in situations where maximum persistence is not necessary. Some of the compounds of formula I can be used at very low rates for plant growth modification, but higher rates may also be useful, depending on factors such as the crop being treated, timing of treatment, etc.

Combinations of the compounds of Formula I with known herbicides also provide effective control of weeds in small graincrops such as wheat and barley. Typical herbicides that may be used are chlortoluron [3-(3-chloro-4-methylphenyl)-1,1-dimethylurea],MCPP [(±)-2-(4-chloro-2-methylphenoxy)propanoic acid], metoxuron [3-(3-chloro-4-methoxyphenyl)-1,1-dimethyl-urea], methabenzthiazuron [1-(benzothiazol-2-yl)-1,3-dimethylurea], dichlofop [(methyl-2-[4-(2,4-dichlorophenoxy)phenoxy]propanoate)], tri-allate[S-2,3-dichloroallyl di-isopropylthiocarbamate], isoproturon-[3-(4-isopropylphenyl)-1,1-dimethylurea], or difenzoquat[1,2-dimethyl-3,5-diphenylpyrazolium ion].

The compounds of Formula I may also be combined with other herbicides and are particularly useful in combination with ureas, such as 3-(3,4-dichlorophenyl)-1,1-dimethylurea, 3-(3,4-dichlorophenyl)-1-methoxy-1-methylurea and 1,1-dimethyl-3-(α,α,α-trifluoro-m-tolyl) urea; the triazines such as 2-chloro-4-(ethylamino)-6-(isopropylamino)-s-triazin; the uracils such as 5-bromo-3-sec-butyl-6-methyluracil; N-(phosponomethyl)glycine; 3-cyclohexyl-1-methyl-6-dimethylamino-s-triazine-2,4(1H,3H)-dione; N,N-dimethyl-2,2-diphenylacetamide; 2,4-dichlorophenoxyacetic acid (and closely related compounds); 4-chloro-2-butynyl-3-chlorophenylcarbamate; diisopropylthiolcarbamic acid, S-(2,3,3-trichloroallyl)ester; ethyl-N-benzoyl-N-(3,4-dichlorophenyl)-2-aminopropionate; 4-amino-6-tert-butyl-3-(methylthio)-1,2,4-triazin-5(4H)-one; 3-isopropyl-1H-2,1,3-benzothiodiazin-(4)-3H-one-2,2-dioxide; α,α,α-trifluoro-2,6-dinitro-N,N-dipropyl-p-toluidine; 1,1'-dimethyl-4,4'-bipyridinium ion; monosodium methanearsonate; and 2-chloro-2',6'-diethyl(methoxymethyl)acetanilide.

The activity of these compounds was discovered in a number of greenhouse tests. The tests are described and the data resulting from them are shown below. The ratings are based on a numerical scale extending from 0=no effect, to 10=maximum effect. The accompanying descriptive symbols have the following meanings:

| | | | |
|---|---|---|---|
| C | = chlorosis or necrosis | 6F | = delayed flowering |
| D | = defoliation | S | = albinism |
| E | = emergence inhibition | | |
| G | = growth retardation | | |
| H | = formative effects | | |
| 6Y | = abscised flowers or buds | | |

TEST A

Seeds of crabgrass (Digitaria spp.), barnyardgrass (Echinochloa crusgalli), wild oats (Avena fatua), cassia (Cassia tora), morningglory (Ipomoea spp.), cocklebur (Xanthium spp.), sorghum, corn, soybean, rice, wheat and nutsedge tubers (Cyperus rotundus) were planted in a growth medium and treated preemergence with a nonphytotoxic solvent solution of the compound of Table III. Other batches of seeds and tubers for all of the foregoing weed and crop plants were planted at the same time as controls. The control plantings were untreated; i.e., neither any compound nor any solvent was applied. At the same time, cotton having five leaves (including cotyledonary ones), bush beans with the third trifoliate leaf expanding, crabgrass with two leaves, barnyardgrass with two leaves, wild oats with two leaves, cassia with three leaves (including cotyledonary ones), morningglory with four leaves (including the cotyledonary ones), cocklebur with four leaves (including the cotyledonary ones), sorghum with four leaves, corn with four leaves, soybean with two cotyledonary leaves, rice with three leaves, wheat with one leaf, and nutsedge with three-five leaves were sprayed with a nonphytotoxic solvent solution of the compound of Table III. Other groups of all the same weed and crop plants were sprayed with the same nonphytotoxic solvent so as to provide control plants. Preemergence and postemergence treated plants and controls were maintained in a greenhouse for sixteen days, then all treated plants were compared with their respective controls and rated visually for response to treatment. The data in Table A shows that the compounds of this invention are effective as herbicides.

TABLE A

POST-EMERGENCE

| Compound | kg/ha | Bushbean | Cotton | Morning-glory | Cockle-bur | Cassia | Nut-sedge | Crab-grass | Barnyard-grass | Wild Oats | Wheat | Corn | Soybean | Rice | Sorghum |
|---|---|---|---|---|---|---|---|---|---|---|---|---|---|---|---|
| Structure 1 (CH₃, Br pyridine; CO₂CH₃, SO₂NHCONH phenyl) | 2/5 | 9C | 6C,9G | 10C | 9C | 5C,9G | 1C,9G | 1C,5G | 1C,3H | 0 | 0 | 1C,5G | 9C | 5C,7G | 2C,9H |
| Structure 2 (C₂H₅, Br pyridine) | 2/5 | 1C | 2C | 3C,9G | 1C | 0 | 1C | 3G | 0 | 0 | 0 | 0 | 0 | 1C | 0 |
| Structure 3 (C₂H₅, OCH₃ pyridine) | 2/5 | 2C,6G,6Y | 3C,3H,5G | 3C,5H | 0 | 2C,4G | 0 | 0 | 0 | 0 | 0 | 0 | 2C,7G | 0 | 0 |
| Structure 4 (CH₃, CH₃ pyridine; N-Cl thiophene) | 2 | 5S,9G,6Y | 2C | 2C | 2C,2H,6F | 2C,5G | 0 | 0 | 2C | 0 | 0 | 2G | 4C,9G | 4C,8G | 2C,7G |
| Structure 5 (CH₃, CH₃ pyridine; SO₂N(CH₃)₂ phenyl) | 2 | 5C,6Y,9G | 3C,3H | 2C | 2C,3H | 2C | 5G | 1C | 2C,6H | 1C | 0 | 3C | 3C | 0 | 2C,8H |

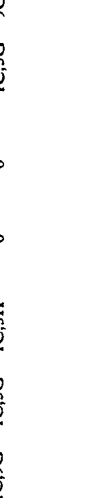

TABLE A-continued

Post-emergence data (continued):

| Compound | kg/ha | Morningglory | Cocklebur | Cassia | Nutsedge | Crabgrass | Barnyardgrass | Wild Oats | Wheat | Corn | Soybean | Rice | Sorghum |
|---|---|---|---|---|---|---|---|---|---|---|---|---|---|
| Pyridine with $CH_3$, $OCH_3$ substituents; $CO_2CH_3$ and $SO_2NHCONH$–phenyl | 2/5 | 9C | 7C,9G | 1C,5G | 5G | 2C | 3C,8H 2G | 1C,5G | 2C,8H | 2C,5G | 1C,3G 1C,6H | 5C,9G | 3C,9G 5C,8G |
| Pyridine with $CH_3$, $CH_3$ substituents; $CO_2CH_3$ and $SO_2NHCONH$–phenyl | 0.4 / 2 | 9D,9G / 3C,9D,9G | 4C,5H / 3C,3H,8G | 8G / 3C,9G | 8G / 1C,8G | 2C,8H / 2C,9G | 2C,8G 8G / 3G 4G | 2C,8H / 2C,9H | 2C / 3C,5G | 1C / 3G | 9H / 9H | 4C,9G / 9C | 2C,9G / 5C,8G | 1C,9G / 2C,9G |

PRE-EMERGENCE

| Compound | kg/ha | Morningglory | Cocklebur | Cassia | Nutsedge | Crabgrass | Barnyardgrass | Wild Oats | Wheat | Corn | Soybean | Rice | Sorghum |
|---|---|---|---|---|---|---|---|---|---|---|---|---|---|
| Pyridine with $CH_3$, Br substituents; $CO_2CH_3$ and $SO_2NHCONH$–phenyl | 2/5 | 9C | 9H | 5C,9G | 10E | 2C | 3C,6G | 3G | 3G | 8H | 9H | 10E | 9H |
| Pyridine with $C_2H_5$, Br substituents; $CO_2CH_3$ and $SO_2NHCONH$–phenyl | 2/5 | 9C | 9H | 0 | 0 | 0 | 0 | 0 | 0 | 2G | 1C | 2G | 1C |
| Pyridine with $C_2H_5$, $OCH_3$ substituents; $CO_2CH_3$ and $SO_2NHCONH$–phenyl | 2/5 | 7G | 8G | 2C | 5G | 2C | 1C,6G | 5G | 3G | 2C,7G | 2C,6H | 3C,8H | 2C,8G |

TABLE A-continued

| Structure | | | | | | | | | | | | |
|---|---|---|---|---|---|---|---|---|---|---|---|---|
| (Cl-pyridyl)SO₂NHCONH-(4,6-dimethylpyridin-2-yl) | 2 | 5H | 0 | — | 0 | 0 | 0 | 0 | 0 | 2G | 1C | 0 |
| (2-SO₂N(CH₃)₂-phenyl)SO₂NHCONH-(4,6-dimethylpyridin-2-yl) | 2 | 9G | 8H | 5C,7G | — | 1C,7G | 5C,9H | 4C,7H | 2C,7G | 1C,9G | 10E | 2C,9H |
| | | | | | | | | 3C,5H | | | | |
| (2-CO₂CH₃-phenyl)SO₂NHCONH-(4-CH₃-6-OCH₃-pyridin-2-yl) | 2/5 | 9G | 9H | 9G | 10E | 2C,5G | 3C,9H | 2C,8G | 1C,6G | 9H | 9H | 10H |
| | | | | | | | | | | | 10E | |
| (2-CO₂CH₃-phenyl)SO₂NHCONH-(4,6-dimethylpyridin-2-yl) | 0.4 | 9G | —  | 9G | 10E | 2G | 2C,9H | 1C,8G | 6G | 9G | 9H | 2C,9H |
| | 2 | 9G | 9G | 5C,9G | 10E | 4G | 9H | 8G | 8G | 9H | 10E | 9H |

Test B

Two bulb pans were filled with fertilized and limed Fallsington silt loam soil. One pan was planted with seeds of corn, sorghum, Kentucky bluegrass and several grassy weeds. The other pan was planted with seeds of soybeans, purple nutsedge tubers (*Cyperus rotundus*), and seeds of several broadleaf weeds. Seeds of the following grassy and broadleaf weeds were planted: crabgrass (*Digitaria sanguinalis*), barnyardgrass (*Echinochloa crusgalli*), wild oats (*Avena fatus*), johnsongrass (*Sorghum halepense*), giant foxtail (*Setaria faberii*), dallisgrass (*Paspalum dilatatum*), cheatgrass (*Bromus secalinus*), mustard (*Brassica arvensis*), cocklebur (*Xanthium pennsylvanicum*), pigweed (*Amaranthus retroflexus*), morningglory (*Ipomoea hederacea*), cassia (*Cassia tora*), teaweed (*Sida spinosa*), velvetleaf (*Abutilon theophrasti*), and jimsonweed (*Datura stramonium*). A smaller pot was also filled with prepared soil and planted with rice and wheat seeds. Another small pot was planted with seeds of sugarbeets. The above four containers were treated preemergence with nonphytotoxic solvent solutions of a compound of this invention (i.e., solutions of said compound were sprayed on the soil surface before seed germination). Duplicates of the above-described seeded containers were prepared without treatment and used as controls.

Twenty-eight days after treatment, the treated and control plants were evaluated and the data recorded as set forth in Table B.

TABLE B

PRE-EMERGENCE ON FALLSINGTON SILT LOAM

| Compound | Rate kg/ha | Crab-grass | Barn-yard-grass | Sor-ghum | Wild Oats | John-son-grass | Dallis-grass | Giant Fox-tail | Ky. Blue-grass | Cheat-grass |
|---|---|---|---|---|---|---|---|---|---|---|
| Ph(CO₂CH₃)(SO₂NHCONH-)-pyridine(CH₃)(CH₃) | 1/16 | 0 | 0 | 4G | 0 | 0 | 0 | 0 | 0 | 3G |
|  | ¼ | 0 | 3G | 3G,5H | 0 | 5H | 0 | 3G | 2G | 5G |
| Ph(CO₂CH₃)(SO₂NHCONH-)-pyridine(CH₃)(Br) | 0.06 | 0 | 0 | 8G,3H | 0 | 5G | 0 | 0 | 0 | 4G |
|  | 0.25 | 0 | 2G | 4G,5H | 4G | 6G | 0 | 0 | 3G | 7G,3C |
| Ph(SO₂N(CH₃)₂)(SO₂NHCONH-)-pyridine(CH₃)(CH₃) | 0.06 | 0 | 0 | 3G | 0 | 0 | 0 | 0 | 0 | 0 |
|  | 0.25 | 0 | 4G | 8G,5H | 3G | 6G,3H | 0 | 2G | 0 | 3G |
| Ph(CO₂CH₃)(SO₂NHCONH-)-pyridine(CH₃)(OCH₃) | 0.06 | 0 | 4G | 8G,3H | 5G | 5G | 0 | 3G | 5G | 7G,5E |
|  | 0.25 | 0 | 5G,3C | 10C | 6G,3C | 8G,8C | 4G | 4G | 6G | 10E |

| Compound | Rate kg/ha | Sugar-beets | Corn | Mus-tard | Cockle-bur | Pig-weed | Nut-sedge | Cotton | Morn-ing-glory | Cassia |
|---|---|---|---|---|---|---|---|---|---|---|
| Ph(CO₂CH₃)(SO₂NHCONH-)-pyridine(CH₃)(CH₃) | 1/16 | 3G | 0 | 4G | 0 | 0 | 0 | 0 | 0 | 0 |
|  | ¼ | 5G,5C | 2G | 7G | 0 | 0 | 3G | 3G | 0 | 0 |
| Ph(CO₂CH₃)(SO₂NHCONH-)-pyridine(CH₃)(Br) | 0.06 | 6G | 0 | 10E | 0 | — | 6G | 0 | 4G | 6G |
|  | 0.25 | 8G,8C | 2G | 10E | 0 | — | 7G,3C | 3G | 7G | 6G |

TABLE B-continued

| PRE-EMERGENCE ON FALLSINGTON SILT LOAM | | | | | | | | | | |
|---|---|---|---|---|---|---|---|---|---|---|
| 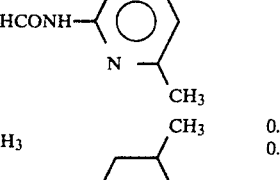 | 0.06 | 0 | 0 | 4G | 0 | 0 | 0 | 0 | 0 | — |
| | 0.25 | 4G | 3G | 8G,5H | 0 | 5G | 0 | 2G | 0 | — |
| 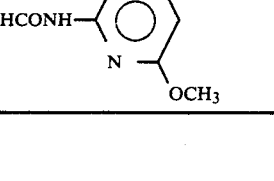 | 0.06 | 10C | 0 | 8G,8C | 2G | 10E | 0 | 4G | 6G | — |
| | 0.25 | 10C | 3G | 10C | 5G | 10E | 3G | 5G,2H | 7G | — |

| | Rate kg/ha | Tea-weed | Velvet-leaf | Jim-son-weed | Soy-bean | Rice | Wheat |
|---|---|---|---|---|---|---|---|
| 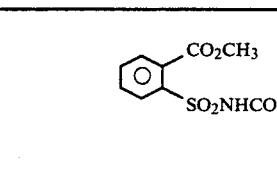 | 1/16 | 0 | 0 | 0 | 0 | 0 | 0 |
| | ¼ | 5G | 0 | 0 | 5G | 6G,5C | 3G |
| 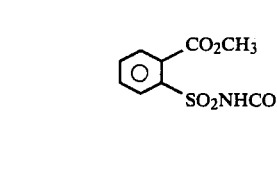 | 0.06 | 2G | 0 | 5G | 2C | 6G,3C | 0 |
| | 0.25 | 7G | 5G | 8G,8C | 7G,5H | 8G,8E | 0 |
| 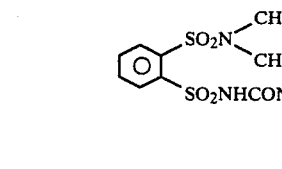 | 0.06 | 0 | 0 | 0 | 0 | 0 | 0 |
| | 0.25 | 0 | 3G | 0 | 2G | 3G | 0 |
| 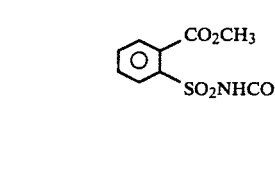 | 0.06 | 5G | 7G,5H | 6G | 3G | 10E | 3G |
| | 0.25 | 8G | 8G,7C | 7G,3C | 6G,5H | 10E | 5G |

Test C

Pots filled with Fallsington silt loam were planted to soybeans, cotton, corn, rice, wheat, sorghum, alfalfa, velvetleaf (*Abutulon theophrasti*), sesbania (*Sesbania exaltata*), cassia (*Cassia tora*), morningglory (Ipomoea spp.), jimsonweed (*Datura stramonium*), cocklebur (*Xanthium pennsylvanicum*), crabgrass (Digitaria spp.), nutsedge (*Cyperus rotunda*), barnyardgrass (*Echinochloa crusgalli*), giant foxtail (*Setaria faberii*), and wild oats (*Avena fatua*). Approximately 2½ weeks after planting, the young plants and the soil around them were sprayed overall with the compound of Example 1 dissolved in a nonphytotoxic solvent. Other groups of all the same weed and crop plants were sprayed with the same nonphytotoxic solvent so as to provide control plants. Fourteen days after treatment, all treated plants were compared with the nonphytotoxic solvent controls and visually rated for response to treatment to give the data presented in Table C.

TABLE C

| Over-the-Top Soil/Foliage Treatment | | | | | | | | |
|---|---|---|---|---|---|---|---|---|
| Rate kg/ha | Soybeans | Velvet-leaf | Sesbania | Cassia | Cotton | Morning-glory | Alfalfa | Jimson-weed | Cockle-bur |

TABLE C-continued

Over-the-Top Soil/Foliage Treatment

| Structure | Rate | | | | | | | | | |
|---|---|---|---|---|---|---|---|---|---|---|
| CO₂CH₃ / SO₂NHCONH–pyridine(CH₃,CH₃) | 1/64 | 9G,5C | 5G,2C | 5G,2C | 0 | 5G,2C | 2G | 5G | 3G | 0 |
| | 1/16 | 10G,8C | 8G,3C | 7G,4C | 4G | 8G,5C | 7G | 5G | 4G | 0 |
| CO₂CH₃ / SO₂NHCONH–pyridine(CH₃,Br) | 1/4 | 10G,7C | 8G,3C | 10G,9C | 7G,4C | 7G,3C | 9G,6C | 8G,4C | 7G,3C | 10G,9C |
| | 1/16 | 10G,5C | 6G,3C | 10G,9C | 6G,3C | 5G,2C | 9G,6C | 7G,3C | 7G,3C | 6G |
| CO₂CH₃ / SO₂NHCONH–pyridine(CH₃,OCH₃) | 1/8 | 10G,5C | 6G,3C | 10G,8C | 7G,3C | 5G,3C | 6G,3C | 3G,1C | 4G,1C | 2G,1C |
| | 1/32 | 10G,5C | 5G,2C | 10G,8C | 5G,2C | 4G,2C | 6G,3C | 1C | 3G,2C | 1G,1C |

| Structure | Rate kg/ha | Corn | Crabgrass | Rice | Nutsedge | Barnyard-grass | Wheat | Giant Foxtail | Sorghum | Wild Oats |
|---|---|---|---|---|---|---|---|---|---|---|
| CO₂CH₃ / SO₂NHCONH–pyridine(CH₃,CH₃) | 1/64 | 3G | 0 | 3G | 0 | 5G | 0 | 0 | 4G,3H | 0 |
| | 1/16 | 3G | 0 | 6G | 0 | 5G | 4G | 0 | 8G,3H | 0 |
| CO₂CH₃ / SO₂NHCONH–pyridine(CH₃,Br) | 1/4 | 0 | 2G,1C | 7G,2C | 9G,4C | 3G,2C | 0 | 2G | 9G,6C | 1G |
| | 1/16 | 0 | 0 | 6G,1C | 9G,4C | 2G,1C | 0 | 0 | 8G,4C | 1G |
| CO₂CH₃ / SO₂NHCONH–pyridine(CH₃,OCH₃) | 1/8 | 0 | 2C | 8G,3C | 2G | 1G | 0 | 2G | 9G,4C | 3G |
| | 1/32 | 0 | 2C | 8G,1C | 2G | 0 | 0 | 0 | 9G,4C | 0 |

Test D

A compound within the scope of the invention was highly active against nutsedge, as is evident from the following test.

Purple nutsedge tubers (*Cyperus rotundus*) were planted about 2 cm deep in Fallsington silt loam contained in plastic pots 10 cm in diameter. Five tubers were put in each pot. A compound of this invention was sprayed dissolved in a non-phytotoxic solvent at a volume rate of 560 l/ha. in four different methods of treatment, i.e., soil surface spray, tuber/soil spray, soil incorporated and post-emergence. For the soil surface spray, the compound was sprayed on the firmed soil surface immediately after planting. For the tuber/soil spray, the compound was sprayed on the exposed tubers and subtending soil before the untreated covering soil was added. The soil incorporation treatment was mixed in the covering soil. The post-emergence treatment was sprayed on the nutsedge foliage and surrounding soil surface after the nutsedge had emerged and had reached the height of about 12 cm.

Immediately after spraying the surface spray, tuber/soil spray and soil incorporated treatments were misted with about 0.3 cm of water over a 90 minute period and then placed in the greenhouse. The post-emergence treatment was placed directly into the greenhouse and watered carefully so that the treatment would not be washed from the foilage.

The following Table D gives results 4 weeks after treating nutsedge with the compound of this invention.

TABLE D

Nutsedge Control

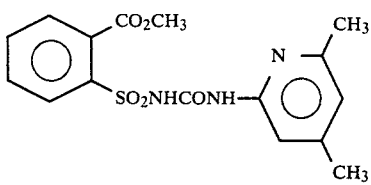

RESPONSE RATING

| Rate kg/ha | Pre-Emerg. Soil Surface | Tuber Spray | Soil Incorp. | Post-Emerg. |
|---|---|---|---|---|
| 1/64 | 0 | 4G | 2G | O |
| 1/16 | 2C,6G | 8G | 9G | 4G |
| ¼ | 4E,9G | 8E,9G | 9E,9G | 3C,6G |

Test E

Two ten-inch in diameter plastic pans lined with polyethylene liners were filled with prepared Fallsington silt loam soil. One pan was planted with seeds of wheat (*Triticum aestivum*), barley (*Hordeum vulgare*), wild oats (*Avena fatua*), downy brome (*Bromus tectorum*), cheatgrass (*Bromus secalinus*), blackgrass (*Alopecurus myosuroides*), annual bluegrass (*Poa annua*), green foxtail (*Setaria viridis*), quackgrass (*Agropyron repens*), Italian ryegrass (*Lolium multiflorum*) and ripgut brome (*Bromus rigidus*). The other pan was planted with seeds of wild buckwheat (*Polygonum convolvulus*), Kochia scoparia, smartweed (*Polygonum pensylvanicum*), Martricaria inodora, tumble mustard (*Sisymbrium altissium*), wild mustard (*Brassica kaber*), tansy mustard (*Descurainia pinnata*), black nightshade (*Solanum nigrum*) and Russian thistle (*Salsola kali*). The above two pans were treated pre-emergence. At the same time, two pans in which the above plant species were growing were treated post-emergence. Plant height at the time of treatment ranged from 1–15 cm depending on plant species.

The compounds applied were diluted with a non-phytotoxic solvent and sprayed over-the-top of the pans. An untreated control and a solvent alone control were included for comparison. All treatments were maintained in the greenhouse for 20 days at which time the treatments were compared to the controls and the effects visually rated. The recorded data are presented in Table E. It is clear from these data that several of the test compounds have utility for weed control in cereal crops.

TABLE E

| Structure | Rate kg/ha | Wheat | Barley | Wild Oats | Downy brome | Cheatgrass | Blackgrass | Annual bluegrass | Green foxtail | Quackgrass | Italian ryegrass | Ripgut brome | Russian thistle | Tansy mustard | Smartweed |
|---|---|---|---|---|---|---|---|---|---|---|---|---|---|---|---|
| CO₂CH₃ / SO₂NHCONH-pyridine(4-CH₃, 2-Br) | 0.015 | 0 | 0 | 0 | 3G | 5G | 1C,3G | 2G | 0 | 0 | 0 | 0 | 0 | 9C,9G | — |
| CO₂CH₃ / SO₂NHCONH-pyridine(4-CH₃, 2-Br) | 0.06 | 0 | 1G | 0 | 3C,4G | 3C,7G | 2C,4G | 5G | 2C,3G | 3G | 1G | 1G | 7C,5G | 10C | — |
| CO₂CH₃ / SO₂NHCONH-pyridine(4-CH₃, 2-OCH₃) | 0.03 | 0 | 2G | 1G | 2C,5G | 3C,6G | 6G | 2C,5G | 2G | 4G | 3G | 3G | 1G | 10C | — |
| CO₂CH₃ / SO₂NHCONH-pyridine(4-CH₃, 2-OCH₃) | 0.125 | 0 | 4G | 2G | 7C,6G | 7C,8G | 6C,7G | 3C,6G | 2C,5G | 7G | 2C,6G | 4G | 5C,6G | 10C | — |
| CO₂CH₃ / SO₂NHCONH-pyridine(4-CH₃, 2-CH₃) | 0.06 | 0 | 0 | 0 | 2C,6G | 4C,6G | 1C,3G | 1G | 2C,2G | 0 | 0 | 0 | 10C | 9C,9G | — |

TABLE E-continued

| Structure | Rate kg/ha | Tumble mustard | Kochia | Shephard's purse | Matricaria inodora | Pre-Emergence Black nightshade | Yellow rocket | Wild mustard | Wild buckwheat |
|---|---|---|---|---|---|---|---|---|---|
| CO2CH3 / SO2NHCONH - pyridine(CH3, CH3) | 0.25 | 0 | 1C,2G | 3C,3G | 7C,8G | 9C,8G | 5C,7G | 1C,3G | 2C,3G | 1C,3G | 1C,2G | 1C,2G | 7C,8G | 9C,9G | — |
| CO2CH3 / SO2NHCONH - pyridine(CH3, Br) | 0.015 | 10C | 3G | 7C,8G | 3C,7G | 8G | 7C,8G | 7C,8G | 2C,3G |
| CO2CH3 / SO2NHCONH - pyridine(CH3, Br) | 0.06 | 10C | 5G | 10C | 8C,9G | 8G | 9C,9G | 9C,9G | 5C,6G |
| CO2CH3 / SO2NHCONH - pyridine(CH3, OCH3) | 0.03 | 10C | 3G | 3C,8G | 5C,8G | 6G | 7C,9G | 9C,8G | 2C,4G |
| CO2CH3 / SO2NHCONH - pyridine(CH3, OCH3) | 0.125 | 10C | 3G | 5C,7G | 6C,7G | 7G | 8G | 10C | 3C,7G |

TABLE E-continued

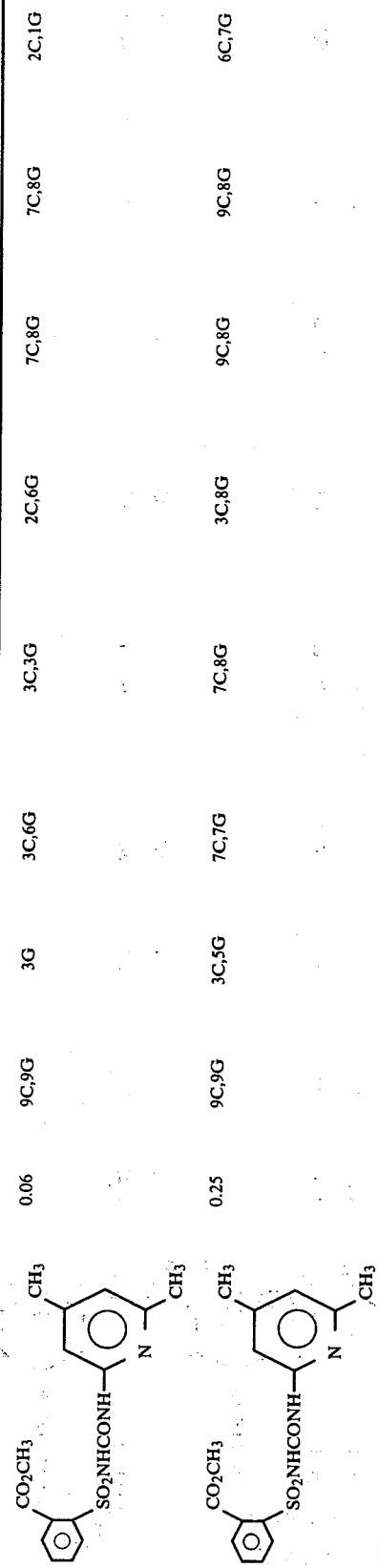

| Structure | Rate kg/ha | Wheat | Barley | Wild Oats | Downy brome | Cheatgrass | Blackgrass | Annual bluegrass | Green foxtail | Quackgrass | Italian ryegrass | Ripgut brome | Russian thistle | Tansy mustard | Smartweed |
|---|---|---|---|---|---|---|---|---|---|---|---|---|---|---|---|
| CH3/CH3 pyridine with CO2CH3, SO2NHCONH | 0.06 | 0 | 9C,9G | 0 | 2C,3G | 3C,6G | 2C,2G | 3C,3G | 3G | 1C,4G | 2C,6G | 7C,8G | 7C,8G | 10C | 2C,1G |
| CH3/CH3 | 0.25 | 0 | 9C,9G | 0 | 3C,5G | 7C,7G | 2C,3G | 7C,8G | 7C,8G | 3C,8G | 9C,8G | 9C,8G | 10C | 10C | 6C,7G |

Post-Emergence

| Structure | Rate kg/ha | Wheat | Barley | Wild Oats | Downy brome | Cheatgrass | Blackgrass | Annual bluegrass | Green foxtail | Quackgrass | Italian ryegrass | Ripgut brome | Russian thistle | Tansy mustard | Smartweed |
|---|---|---|---|---|---|---|---|---|---|---|---|---|---|---|---|
| CH3/Br | 0.015 | 0 | 0 | 0 | 3C,5G | 4C,7G | 2C,3G | 4G | 1C,5G | 2G | 1G | 1G | 10C | 10C | — |
| CH3/Br | 0.06 | 0 | 1G | 1C,1G | 2C,3G | 2C,6G | 2C,5G | 1C,3G | 2G | 1C,2G | 3G | 2G | 10C | 10C | — |
| CH3/OCH3 | 0.03 | 0 | 1G | 0 | | | | | | | 1G | 1G | 10C | 10C | — |

TABLE E-continued

| Structure | Rate kg/ha | Tumble mustard | Kochia | Shephard's purse | Matricaria inodora | | | | Yellow rocket | Wild mustard | Wild buckwheat |
|---|---|---|---|---|---|---|---|---|---|---|---|
| CO₂CH₃ / SO₂NHCONH-pyridine(CH₃, OCH₃) | 0.125 | 0 | 2C,3G | 1C,2G | 4C,5G | 4C,7G | 3C,6G | 2C,5G | 2C,4G | 1C,3G | 1C,2G | 2C,3G | 10C | 10C | — |
| CO₂CH₃ / SO₂NHCONH-pyridine(CH₃, CH₃) | 0.06 | 0 | 0 | 0 | 1G | 2G | 0 | 0 | 0 | 0 | 0 | — | 9C,7G | — |
| CO₂CH₃ / SO₂NHCONH-pyridine(CH₃, CH₃) | 0.25 | 0 | 1C,2G | 0 | 5C,4G | 4C,4G | 1C,2G | 0 | 0 | 0 | 2C,2G | 10C | 10C | — |

| | Rate | | | | | Post-Emergence | | | |
|---|---|---|---|---|---|---|---|---|---|
| Structure | kg/ha | Tumble mustard | Kochia | Shephard's purse | Matricaria inodora | Black nightshade | Yellow rocket | Wild mustard | Wild buckwheat |
| CO₂CH₃ / SO₂NHCONH-pyridine(CH₃, Br) | 0.015 | 10C | 3C,5G | 2C,3G | 9C,8G | 1C,4G | 10C | 10C | 2C,3G |
| CO₂CH₃ / SO₂NHCONH-pyridine(CH₃, Br) | 0.06 | 10C | 7C,8G | 3C,3G | 10C | 3C,6G | 10C | 10C | 2C,4G |

TABLE E-continued

| Structure | | | | | | | | | |
|---|---|---|---|---|---|---|---|---|---|
| ![structure with CO2CH3, SO2NHCONH, pyridine CH3, OCH3] | 0.03 | 10C | 0 | 7C,6G | 10C | 2C,5G | 10C | 10C | 1C,2G |
| ![structure with CO2CH3, SO2NHCONH, pyridine CH3, OCH3] | 0.125 | 10C | 2C,3G | 8C,7G | 10C | 2C,6G | 10C | 10C | 2C,4G |
| ![structure with CO2CH3, SO2NHCONH, pyridine CH3, CH3] | 0.06 | 10C | 7C,8G | 1C,1G | 0 | 1G | 4C,5G | 10C | 0 |
| ![structure with CO2CH3, SO2NHCONH, pyridine CH3, CH3] | 0.25 | 10C | 1C,2G | 2G | 2C,3G | 3G | 7C,8G | 10C | 0 |

What is claimed is:

1. A compound of the formula:

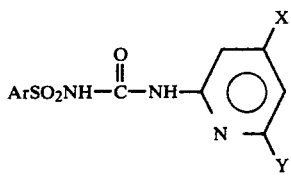

wherein
X is CH$_3$—, CH$_3$CH$_2$— or CH$_3$O;
Y is CH$_3$—, CH$_3$CH$_2$—, CH$_3$O—, CH$_3$CH$_2$O—, Cl, Br or F;
Ar is

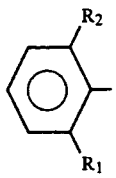

R$_1$ is CO$_2$R$_4$;
R$_2$ is H;
R$_4$ is C$_1$-C$_4$ alkyl, C$_3$-C$_4$ alkenyl, ClCH$_2$CH$_2$— or CH$_3$OCH$_2$CH$_2$.

2. A compound of claim 1 wherein R$_1$ is CO$_2$R$_4$ wherein R$_4$ is C$_1$-C$_3$ alkyl or allyl.

3. A compound of claim 1 wherein R$_1$ R$_2$ is Cl.

4. A compound of claim 1 wherein Y is Cl, Br, CH$_3$— or CH$_3$O—.

5. A compound of claim 2 wherein Y is Cl, Br, CH$_3$— or CH$_3$O—.

6. The compound of claim 1, 2-[[(4,6-dimethyl-2-pyridinyl)aminocarbonyl]aminosulfonyl]benzoic acid, methyl ester.

7. The compound of claim 1, 2-[[(6-methoxy-4-methyl-2-pyridinyl)aminocarbonyl]aminosulfonyl]benzoic acid, methyl ester.

8. The compound of claim 1, 2-[[(6-bromo-4-methyl-2-pyridinyl)aminocarbonyl]aminosulfonyl]benzoic acid, methyl ester.

9. A composition suitable for controlling the growth of undesired vegetation which comprises an effective amount of a compound of claim 1 and at least one of the following: surfactant, an inert solid or liquid diluent.

10. A composition suitable for controlling the growth of undesired vegetation which comprises an effective amount of a compound of claim 2 and at least one of the following: surfactant, an inert solid or liquid diluent.

11. A composition suitable for controlling the growth of undesired vegetation which comprises an effective amount of a compound of claim 3 and at least one of the following: surfactant, an inert solid or liquid diluent.

12. A composition suitable for controlling the growth of undesired vegetation which comprises an effective amount of a compound of claim 4 and at least one of the following: surfactant, an inert solid or liquid diluent.

13. A composition suitable for controlling the growth of undesired vegetation which comprises an effective amount of a compound of claim 5 and at least one of the following: surfactant, an inert solid or liquid diluent.

14. A composition suitable for controlling the growth of undesired vegetation which comprises an effective amount of a compound of claim 6 and at least one of the following: surfactant, an inert solid or liquid diluent.

15. A composition suitable for controlling the growth of undesired vegetation which comprises an effective amount of a compound of claim 7 and at least one of the following: surfactant, an inert solid or liquid diluent.

16. A composition suitable for controlling the growth of undesired vegetation which comprises an effective amount of the compound of claim 8 and at least one of the following: surfactant, an inert solid or liquid diluent.

17. A method for controlling the growth of undesired vegetation which comprises applying to the locus to be protected an effective amount of a compound of claim 1.

18. A method for controlling the growth of undesired vegetation which comprises applying to the locus to be protected an effective amount of a compound of claim 2.

19. A method for controlling the growth of undesired vegetation which comprises applying to the locus to be protected an effective amount of a compound of claim 3.

20. A method for controlling the growth of undesired vegetation which comprises applying to the locus to be protected an effective amount of a compound of claim 4.

21. A method of controlling the growth of undesired vegetation which comprises applying to the locus to be protected an effective amount of a compound of claim 5.

22. A method for controlling the growth of undesired vegetation which comprises applying to the locus to be protected an effective amount of a compound of claim 6.

23. A method for controlling the growth of undesired vegetation which comprises applying to the locus to be protected an effective amount of a compound of claim 7.

24. A method for controlling the growth of undesired vegetation which comprises applying to the locus to be protected an effective amount of the compound of claim 8.

* * * * *